(12) United States Patent
Tanzer et al.

(10) Patent No.: US 7,001,741 B1
(45) Date of Patent: Feb. 21, 2006

(54) DETECTION OF PEROXIDASE ACTIVITY IN MILK OR MILK PRODUCTS

(75) Inventors: Dieter Tanzer, Ober-Ramstadt (DE); Karl-Dieter Krenn, Pfungstadt (DE)

(73) Assignee: Merck Patent GmbH, Darmstadt (DE)

( * ) Notice: Subject to any disclaimer, the term of this patent is extended or adjusted under 35 U.S.C. 154(b) by 428 days.

(21) Appl. No.: 10/148,267

(22) PCT Filed: Nov. 13, 2000

(86) PCT No.: PCT/EP00/11200

§ 371 (c)(1),
(2), (4) Date: Oct. 15, 2002

(87) PCT Pub. No.: WO01/40501

PCT Pub. Date: Jun. 7, 2001

(30) Foreign Application Priority Data

Nov. 29, 1999 (DE) ................................ 199 57 367

(51) Int. Cl.
*C12Q 1/28* (2006.01)
(52) U.S. Cl. ........................................ 435/28
(58) Field of Classification Search ................ 435/25
See application file for complete search history.

(56) References Cited

U.S. PATENT DOCUMENTS 4,755,472 A  12/1980  Yip et al.

FOREIGN PATENT DOCUMENTS

EP  0832985 A  4/1998
WO  WO 8002800 A  12/1980

OTHER PUBLICATIONS

Josephy et al., "Cooxidation of the clinical reagent 3,3',5, 5'-tetramethylbenzidine by prostaglandin synthase", Cancer Research 42 (7) : 2567-70 (1982).*

* cited by examiner

*Primary Examiner*—Sandra E. Saucier
(74) *Attorney, Agent, or Firm*—Millen, White, Zelano, Branigan, P.C.

(57) ABSTRACT

The invention relates to an agent and a method for the dry chemical detection of lactoperoxidase in milk or dairy products. The method according to the invention is characterized by rapid execution thereof and said method has a high degree of sensitivity. The high detection sensitivity is achieved by adding iodide ions to the usual reagents.

11 Claims, 4 Drawing Sheets

DETECTION OF PEROXIDASE ACTIVITY IN MILK OR MILK PRODUCTS

Figure 1:
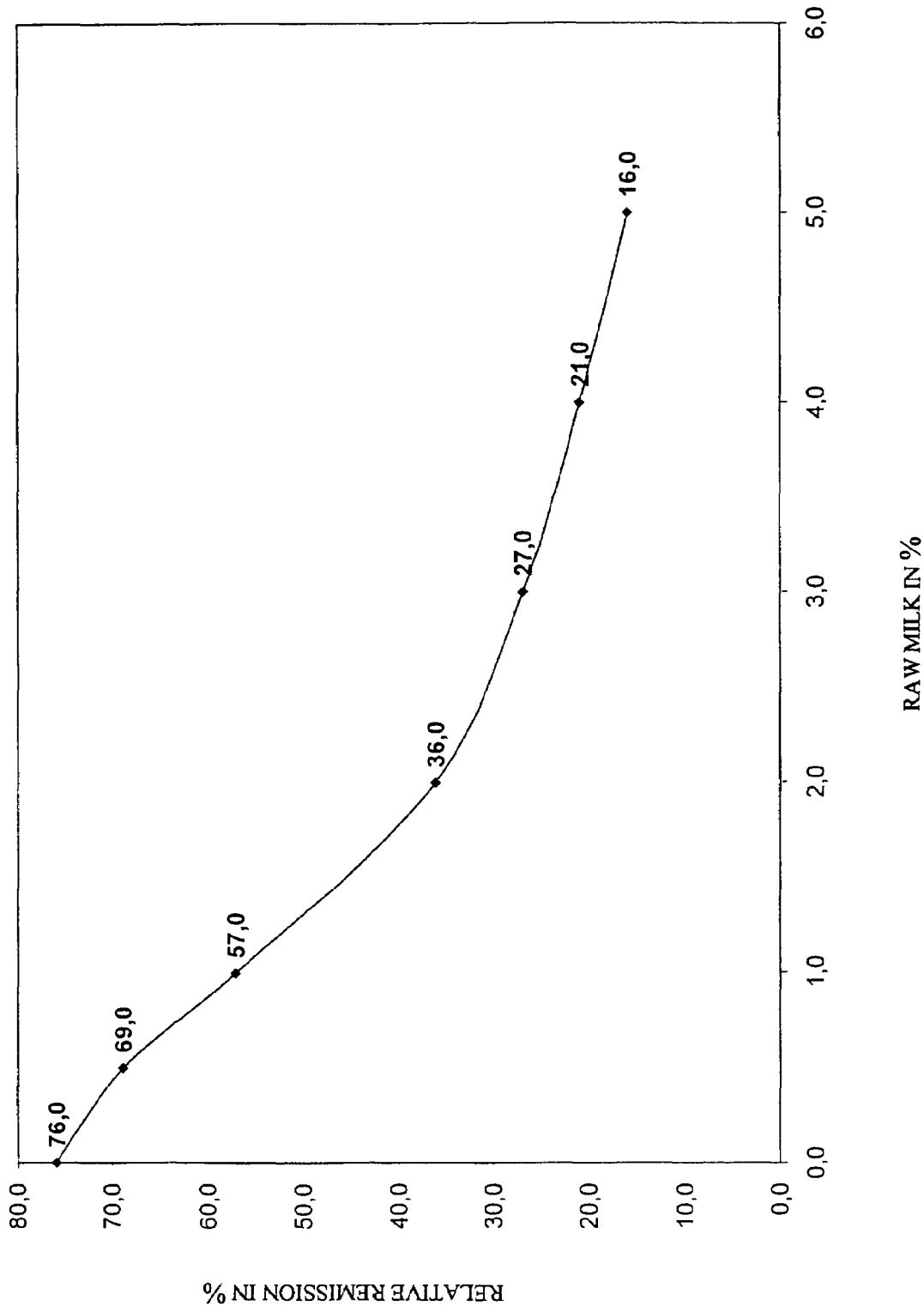

The invention relates to a method and a composition for the rapid detection of peroxidases in milk and milk products.

Thermal treatment has a crucial effect on the quality and hygiene of food milk. The main aim of heat treatment is to kill pathogenic microorganisms or agents which cause spoilage. However, the treatment also results in changes to further milk constituents, such as, for example, deactivation of enzymes inherent in milk. The heating conditions therefore have to be set in such a way that desired properties are achieved in the end product without undesired side effects being produced at the same time.

The temperature/time ranges for the production of various types of milk are stipulated in German federal milk regulations (Verordnung über Hygiene-und Qualitätsanforderungen an Milch und Erzeugnisse auf Milchbasis [Regulation on Hygiene and Quality Requirements of Milk and Milk-Based Products] (milk regulation) of 24 Apr. 1995 (in H. Loos and T. Nebe: Das Recht der Milchwirtschaft in der Bundesrepublik Deutschland [Dairy Law in the Federal Republic of Germany], Babd V, pp. 27–28, Behr's Verlag, Hamburg (supplement 130 of 31 Dec. 1997)). Pasteurisation, ultra-heat treatment (UHT) and sterilisation are recognised heat-treatment methods. Longtime heating, short-time heating and high-temperature heating are further differentiation criteria for pasteurised milk.

For the control and characterisation of heat-treated milk, use is made, inter alia, of the temperature-dependent deactivation of enzymes inherent in milk (M. W. Griffiths, J. Food Protection, 49 (1986), pp. 696–705; M. Villamiel et al., Z. Lebensm. Unters. Forsch. 208 (1999), pp. 169–171). Whereas the detection of alkaline phosphatase is employed for the monitoring of adequate long-time heating or short-time heating, the measurement of peroxidase inherent in milk (lactoperoxidase) enables an assessment of correct high-temperature heating. Accordingly, the activity of the original milk enzyme alkaline phosphatase must be negative and the activity of the milk enzyme lactoperoxidase must be positive in short-time heated milk, while both enzymes must be deactivated in high-temperature-heated milk.

In addition, technical defects in plants can result in mixing of heat-treated milk or heat-treated milk products with insufficiently heated milk or insufficiently heated milk products during heat treatment, which must be checked using suitable test methods.

The increasing significance of quality control with regard to the thermal treatment of milk becomes clear with the coming into force of European Directive 92/46. The prerequisite for functioning quality control and definition of limit values is the existence of suitable analytical methods which enable rapid and reliable checking of quality-relevant criteria and compliance with the goods declaration (pasteurised milk/UHT milk).

The activity of the enzymes inherent in milk is generally determined using colour reactions. The enzymes catalyse the reaction (redox reaction, hydrolysis) of suitable substrates, accompanied by a colour change. Qualitative, semi-quantitative or quantitative evaluation of the colour change can be carried out by means of visual or spectrometric methods.

Various methods are known in the prior art for determining the activity of lactoperoxidase. The substrates employed are, for example, guaiacol, 1,4-phenylenediamine, N,N-dimethyl-p-phenylenediamine dihydrochloride, o-tolidine, o-dianisidine, 2,2'-azinodi(3-ethylbenzothiazoline-6-sulfonic acid), 2,7-diaminofluorene, benzidine and 3,3',5,5'-tetramethylbenzidine. Only a few reagents, such as reagents based on guaiacol and phenylenediamine, have official approval as detection reagent (substrate) for correct pasteurisation of milk by high-temperature heating. Examples are the Guajakreagenz Neu®, the Hocherhitzungsreagenz (high-temperature heating reagent) N3® and Traventol®.

The disadvantage of these methods is that they have to be carried out by wet-chemical methods, i.e. the detection reaction has to be carried out in solution. A number of reagent solutions, some of which are toxic, are added to the sample, with the consequence of corresponding handling and disposal problems.

Analysis using solid, sorptive supports, so-called test strips, has recently increased in importance. The main advantages of these dry-chemical methods include, in particular, simple handling and unproblematic disposal owing to the small amounts of reagent. Most or preferably even all of the reagents necessary for the detection reaction are embedded in corresponding layers of a solid, sorptive or swellable support to which the sample is applied. After contact of the reaction zone with the sample, the detection reaction proceeds. The colour formed is a measure of the amount or activity of the analyte to be determined and can be evaluated visually or by means of simple reflectometers.

The literature discloses a multiplicity of different methods, including dry-chemical ones, for determining the activity of peroxidases and other peroxidatively active substances. The determination is of major significance for biochemical analysis and medical diagnostics, in particular in combination with immunoassays (peroxidase labelling) (K. M. Pruitt et al., Anal. Biochem. 191 (1990), 278–286).

By contrast, no methods are known for the detection of lactoperoxidase which meet the above-mentioned demands with respect to speed and sensitivity. The existing methods for the detection of lactoperoxidase in milk prove to be of low or zero suitability for rapid and reliable quality control since most of them suffer from a number of the following disadvantages:

The reagents necessary have to be combined in precisely defined concentrations in accordance with a handling procedure, which results in considerable expenditure of time.

Handling of reagent solutions which are in some cases not stable on storage and therefore have to be freshly prepared regularly (low practicability, disposal problems).

In particular in the case of photometric evaluation, high equipment complexity, associated with high analysis costs, is necessary.

Trained personnel and suitable laboratory equipment are necessary.

Interferences in the measurement by the matrix milk (inherent colour and cloudiness) require additional sample preparation with the risk of false negative findings or low peroxidase findings (incomplete recovery).

Complex calibration in visual methods by comparison with peroxidase standard solutions. Horseradish peroxidase is frequently used here. However, there is no guarantee of comparability with lactoperoxidase.

EP 0 832 985 describes a method for the detection of lactoperoxidase or alkaline phosphatase which is carried out on a solid support. The dry-chemical procedure avoids some of the above-mentioned disadvantages. However, the experiment is very time-consuming to carry out, with a duration of from 20 to 60 minutes. In addition, the detection sensitivity of the method, as in most wet-chemical methods, is too low.

As a sensitivity which is adequate for the user, the detection of at least 1% of raw milk in peroxidase-free milk (for example UHT milk) is to be aimed at.

The present invention is therefore based on the object of providing a method for the determination of lactoperoxidase in milk or milk products which is simple and fast to carry out, is specific and is inexpensive and at the same time guarantees the requisite sensitivity. In addition, the method according to the invention should be suitable for evaluation using a reflectometer.

Surprisingly, it has been found that a specific and highly sensitive detection system for lactoperoxidase in the presence of hydrogen peroxide is obtained if the usual substrates and buffers for peroxidase detection are employed and in addition a certain amount of iodide ions is added.

Whereas the addition of iodide ions results in a significant reduction in the detection sensitivity for horseradish peroxidase, the addition of iodide ions causes a significant increase in the detection sensitivity in relation to lactoperoxidase.

The addition of iodide ions must be balanced precisely here since excessive amounts result in an undesired side reaction. Without a substrate, no colour change is observed even in the presence of very high iodide concentrations. The deliberate addition of a certain amount of iodide ions thus enables the provision of an adequately sensitive measurement system for lactoperoxidase in milk or milk products. In order to ensure that the experiment is carried out rapidly and consumption of reagents is low, the method according to the invention is preferably carried out by dry-chemical methods.

The invention relates to a composition for the detection of lactoperoxidase consisting of a support to which at least one peroxidase substrate and an iodide have been applied.

In a preferred embodiment of the composition according to the invention, the substrate located on the support is 1,4-phenylenediamine, 2,2'-azinobis(3-ethylbenzothiazole-6-sulfonic acid) or 3,3',5,5'-tetramethylbenzidine.

The invention relates to a method for the determination of lactoperoxidase in milk or milk products which is characterised by the following reaction steps:
  a) provision of a support to which at least one peroxidase substrate and an iodide have been applied;
  b) optionally, if necessary, addition of reagents which are unstable on the support, such as, for example, a peroxide former, to the sample;
  c) brief immersion of the support into the sample;
  d) waiting for the colour reaction;
  e) detection of the colour reaction.

In a preferred embodiment of the method according to the invention, the peroxide former added in step b) is hydrogen peroxide.

In a preferred embodiment of the method according to the invention, the detection of the colour reaction in step e) is carried out by reflectometry. The present invention furthermore relates to the use of the composition and the method according to the invention for the determination of the activity of lactoperoxidase in high-temperature-heated milk.

FIG. 1 depicts the correlation between the measured relative remission (%) and the proportions of raw milk. The proportion of raw milk in % is plotted on the abscissa, and the relative remission in % on the ordinate.

Figure 2:
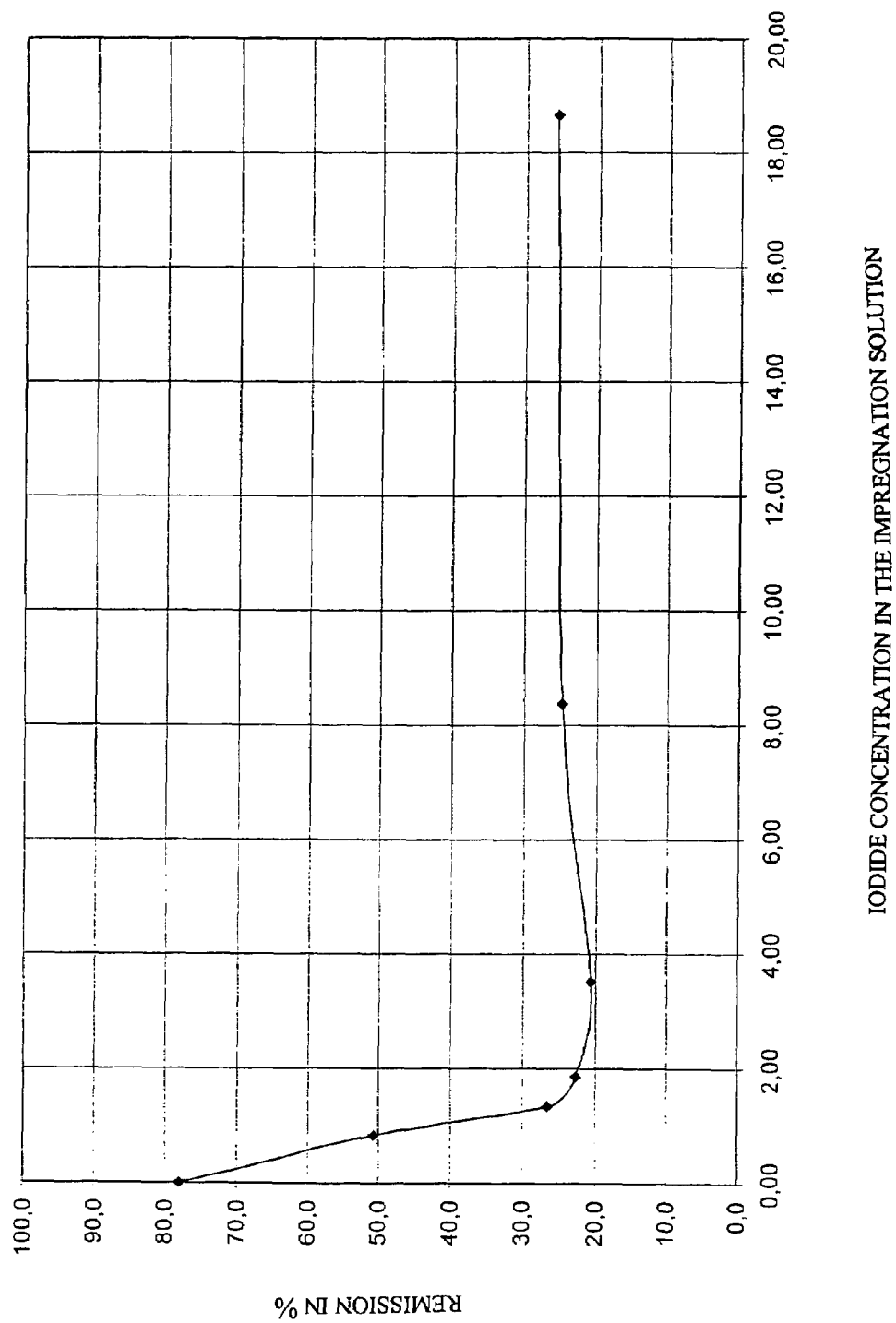

FIG. 2 shows the addition of iodide. The proportion of raw milk and thus the peroxidase content was kept constant at 5%. The iodide concentration in the impregnation solution is plotted on the abscissa and the remission in % on the ordinate.

Figure 3:
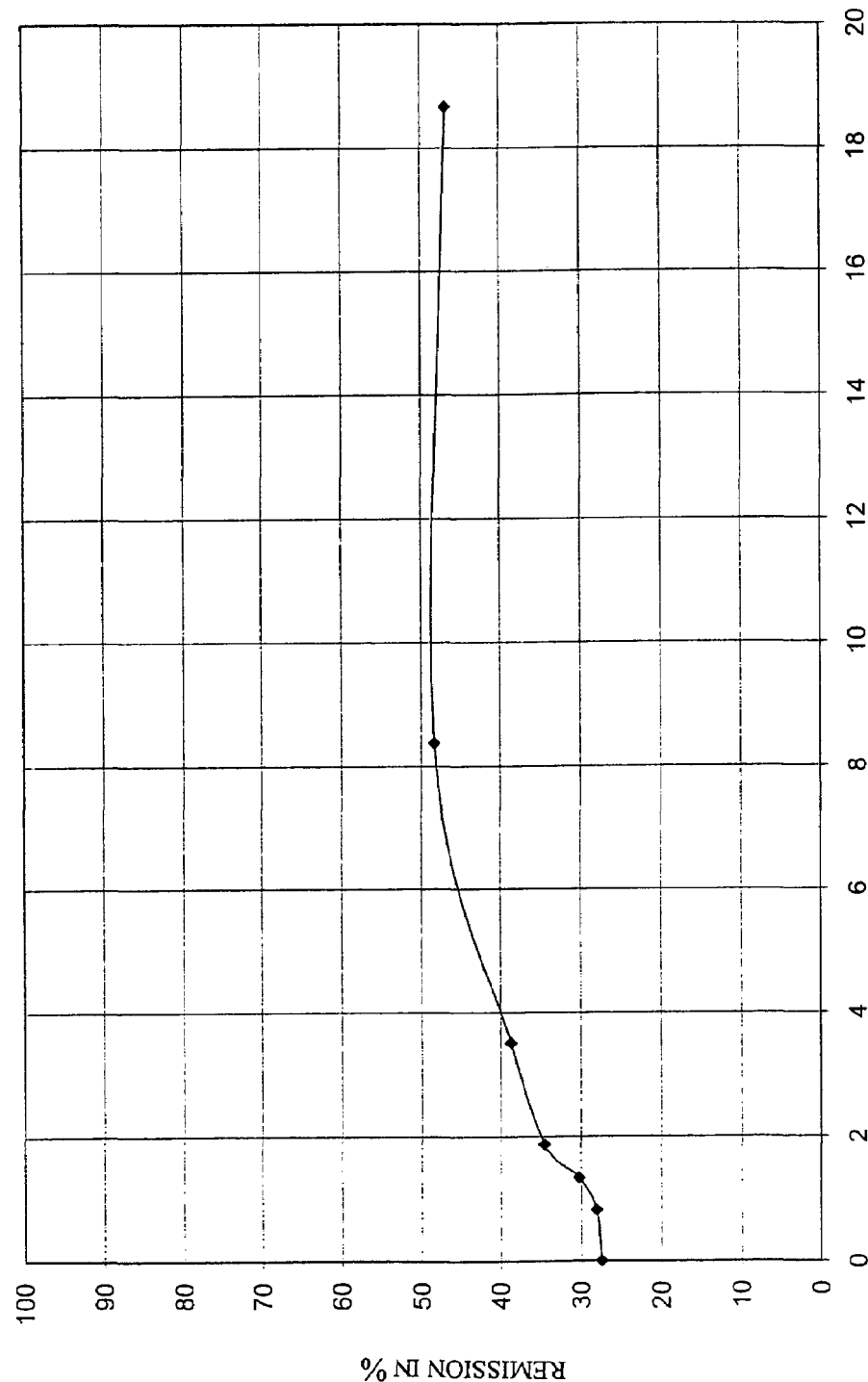

FIG. 3 depicts the effect of the iodide content on the sensitivity of the detection system for horseradish peroxidase. The iodide concentration in the impregnation solution is plotted on the abscissa and the remission in % on the ordinate.

Figure 4:
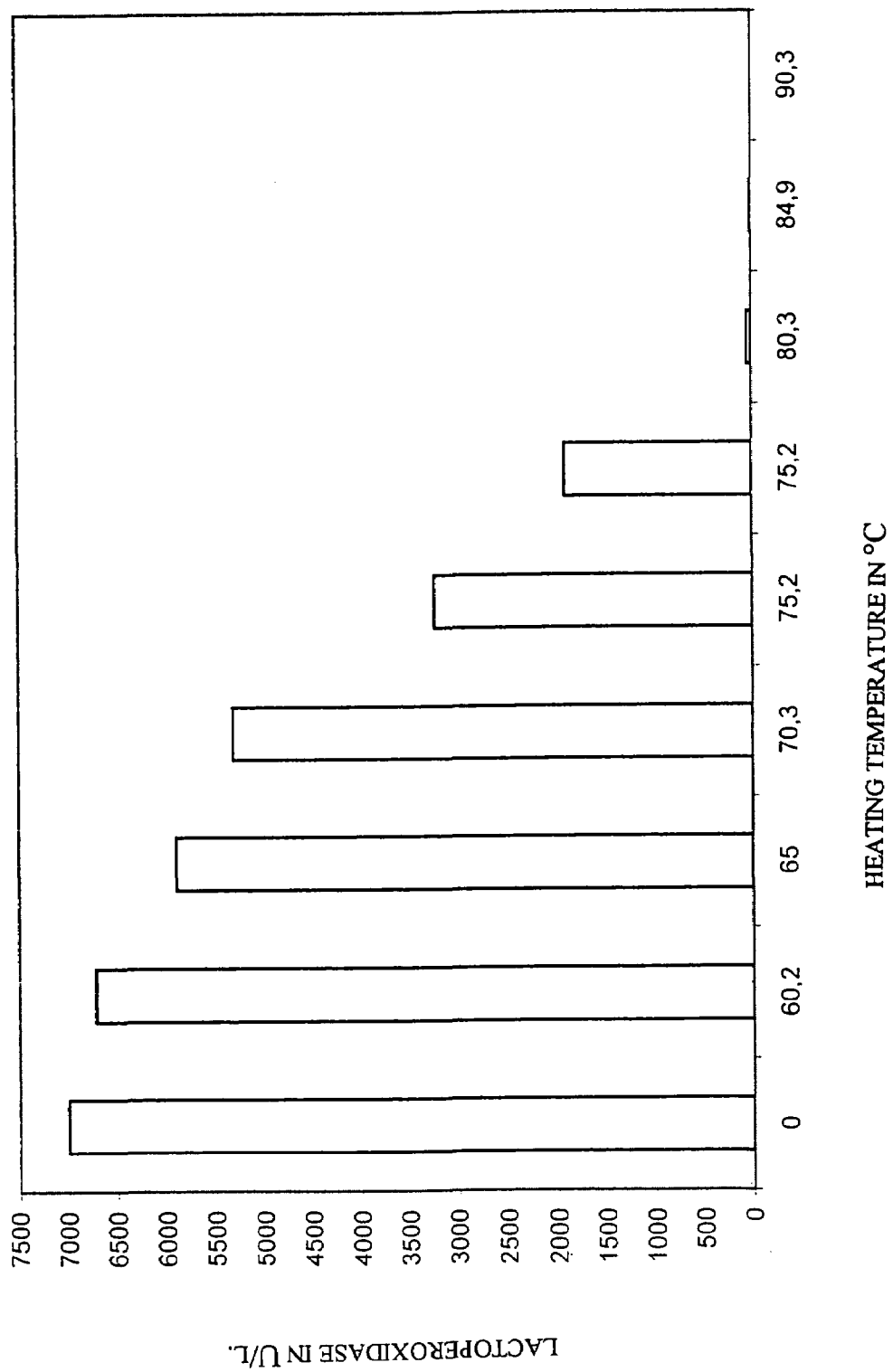

FIG. 4 depicts test strips from Example 1 dipped into milk heat-treated in various ways and analysed as described in Example 1. The heating temperature in ° C. is plotted along the abscissa. The ordinate indicates the remaining activity of the lactoperoxidase in U/l.

The essential prerequisite for achieving the desired detection sensitivity is the addition of iodide ions. Suitable iodides are, for example, the alkali metal iodides and ammonium iodide, preferably lithium iodide. The optimum iodide concentration must be matched to the conditions of the detection system. The person skilled in the art is capable of determining this concentration by means of a few experiments (in this respect, see Example 2). The iodide concentration in the solution with which the support is impregnated is typically between 1.5 and 8 mmol/l, particularly preferably between 3 and 4 mmol/l.

Substrates which can be employed are all reagents or reagent combinations which are known in the literature for the detection of peroxidases and which result in suitable colour changes and facilitate sensitive detection. These are preferably 1,4-phenylenediamine, 2,2'-azinobis(3-ethylbenzothiazole-6-sulfonic acid) and particularly preferably 3,3',5,5'-tetra-methylbenzidine.

The peroxide formers employed in accordance with the invention for applications of this type are known substances, such as, for example, hydrogen peroxide/urea and particularly preferably hydrogen peroxide. It is likewise possible to generate hydrogen peroxide in situ, for example by the known reaction of glucose with glucose oxidase.

The pH of the detection system must be set in such a way that on the one hand the enzyme is able to develop its maximum activity, and on the other hand the most favourable pH for the colour reaction (dependent on the substrate) is present. For the method according to the invention, buffer substances are therefore optionally also added to the reagent system, particularly in the case of milk products, in order to enable the reaction to proceed in an optimum pH range. Suitable sample buffers are those which set the pH to about 5.0–7.0. The pH range 6.0–7.0 is preferred. Possible buffers are, for example, phosphate buffers.

The test system is preferably in the form of an impregnated matrix, i.e. substantially all the reagents necessary for the detection (substrate, iodide, peroxide former and optionally buffer), where appropriate also stabilisers and solubilisers, are embedded in a sorptive support. The support is immersed directly into the sample to be investigated, and the colour reaction is followed in a suitable manner. In exceptional cases, substances which, for example, are not sufficiently stable on the support have to be added in the form of a solution. The person skilled in the art is capable of adding reagents of this type in suitable concentrations. On use of hydrogen peroxide, for example, a corresponding solution is added to the sample just before immersion of the test strip (step b of the method according to the invention). Preferably, however, all the reagents are embedded on the support. In this case, step b) of the method according to the invention is superfluous.

Sorptive supports which can be used are all materials which are usually used for tests of this type. The most widespread is the use of filter paper, but it is also possible to employ other sorptive cellulose or plastic products. The sorptive supports are impregnated in a known manner with impregnation solutions which contain the reagents necessary for the determination of peroxidase. The impregnated and dried papers can be cut to size in a suitable manner and stuck or heat-sealed onto support films in a known manner.

The detection of the colour reaction is carried out by spectrophotometry, visually or preferably by reflectometry.

If not all the substances which are necessary for the peroxidase detection are present on the test strips according to the invention, it is possible to assemble a test kit which, besides the test strip, contains the substances or solutions of the substances which additionally have to be added to the sample.

In order to carry out the method according to the invention, the milk sample to be investigated is diluted with buffer solution or preferably with deionised water in accordance with the expected activity of the peroxidase. A 1:5 dilution is typically sufficient. A solution containing hydrogen peroxide is preferably subsequently added to the sample. The content of hydrogen peroxide in the sample solution is typically between 0.005 and 1%, preferably between 0.01 and 0.1%.

After brief mixing, a suitably prepared test strip is immediately dipped briefly into the solution. Excess solution is generally then easily removed from the support, and the colour reaction is awaited. After passage of a certain reaction time, typically between 1 and 5 minutes, the test strip is evaluated, preferably by reflectometry. On use of a peroxide former, which may be applied to the test strip, the prior addition of hydrogen peroxide is superfluous.

Typically, about 3–5 minutes are required to carry out the method according to the invention.

On use of the method according to the invention, it has been observed that usual calibration methods are not sufficiently accurate. For example, calibration with lactoperoxidase standard solutions (prepared by dissolution of commercial freeze-dried lactoperoxidase), as frequently described in the literature (for example EP 0 832 985), has proven not to be comparable with practice and thus as unsuitable since significantly different lactoperoxidase activities are obtained in this procedure. In order to evaluate the colour reactions of the method according to the invention, standard solutions are therefore prepared from peroxidase-free milk to which various amounts of fresh raw milk are added.

It has furthermore been observed that calibration with horseradish peroxidase is unsuitable for the method according to the invention. Whereas the method according to the invention greatly increases the detection sensitivity for lactoperoxidase, a converse effect occurs for horseradish peroxidase.

However, it has been found that the method according to the invention is likewise suitable for analysing the peroxidase content of certain vegetables or of cereals. Before freezing, vegetables have to be subjected to heat treatment (blanching), in particular with the aim of eliminating undesired enzyme activities and increasing the storage stability. The efficacy of this treatment can be monitored in a suitable manner by means of a peroxidase test (B. P. Wassermann and J. D. Wagner, 13 (2), 1985, pp. 84–85). Detection by means of the method according to the invention is likewise suitable. Further details are given in Example 5.

The method according to the invention thus offers the possibility of rapid and sensitive detection of certain peroxidases, particularly lactoperoxidase. Using the officially approved Traventol® reagent, it is possible, given a trained eye, to detect, for example, only about 3% of raw milk in peroxidase-free milk (E. Olszewski and H. Reuter, Z. Lebensm. Unters. Forsch. 194 (1992), pp. 235–239). Using the method according to the invention, contents of raw milk in peroxidase-free milk which are significantly below 1%, often even below 0.5%, can typically be detected.

Due to the embedding of the reagents on a support, performance of the peroxidase detection according to the invention is greatly simplified and the amount of reagents reduced.

The detection preferably by reflectometry does not require complex equipment and at the same time gives more accurate results than a visual evaluation.

Even without further comments, it is assumed that a person skilled in the art will be able to utilise the above description in the broadest scope. The preferred embodiments and examples should therefore merely be regarded as descriptive disclosure which is absolutely not to be regarded as limiting in any way.

The complete disclosure content of all applications, patents and publications mentioned above and below, in particular the corresponding application DE 199 57 367, filed on 29 Nov. 1999, is incorporated into this application by way of reference.

EXAMPLES

Unless otherwise stated, all reagents were purchased from Merck KGaA.

1. Determination of Peroxidase Using Test Strips—Evaluation of the Reaction Colour by Reflectometry:

Production of the Test Strips:

A filter paper (Binzer, 1450 CV acid-washed) is impregnated with the impregnation solution below and dried with warm air after the impregnation. The paper is heat-sealed onto a white support film using hot-melt adhesive (for example Technomelt Q® 3273 from Henkel, Düsseldorf) and cut into strips in a suitable manner giving a reaction zone of about 6 mm×8 mm.

Composition of the Impregnation Solution:

5.0 g of malonic acid, 2.0 g of 3,3',5,5'-tetramethylbenzidine and 0.45 g of lithium iodide are dissolved in 1 l of ethanol (96%).

Preparation of the Standard Solutions:

Various amounts of fresh raw milk are added to peroxidase-free milk prepared by heating fresh raw milk giving standard solutions in the range 0–5% of raw milk, based on peroxidase-free milk.

Calibration with lactoperoxidase standard solutions (prepared by dissolving commercial freeze-dried lactoperoxidase in peroxidase-free milk), as frequently described in the literature (for example EP 0 832 985 A2), has proven not to be comparable with practice and thus as unsuitable since significantly different lactoperoxidase activities are obtained in this procedure.

Analysis:

For analysis, the milk samples obtained are diluted 1:5 with deionised water. 5 drops (about 0.25 ml) of 0.3% hydrogen peroxide solution are added to 5 ml of the diluted sample. The test strips are immediately immersed into the samples.

Depending on the concentration of peroxidase, blue colorations of varying intensity form, which can be evaluated visually by comparison with a colour card. For quantitative evaluation, the test strips are evaluated after precisely 3 minutes in a small hand diode-based reflectometer (RQflex® reflectometer from Merck KGaA).

The correlation between the measured relative remission (%) and the proportions of raw milk is shown in FIG. 1. The proportion of raw milk in % is plotted on the abscissa, and the relative remission in % on the ordinate. Raw milk proportions of 0.5% result in a significant blue coloration and can be detected reliably using the method. The method is thus significantly more sensitive than existing methods.

2. Effect of the Iodide Content on the Sensitivity of the Detection System for Lactoperoxidase:

The test strips were prepared and evaluated as described in Example 1. The iodide concentration was varied. The proportion of raw milk and thus the peroxidase content was kept constant at 5%. Addition of iodide results, as can be seen in FIG. 2, in a significant increase in the detection sensitivity. At iodide concentrations above about 8 mmol/l, the reaction colour is masked by a non-specific blue coloration as a consequence of an undesired side reaction. In FIG. 2, the iodide concentration in the impregnation solution is plotted on the abscissa and the remission in % on the ordinate.

3. Effect of the Iodide Content on the Sensitivity of the Detection System for Horseradish Peroxidase:

Test strips from Example 2 with various iodide concentrations were dipped into an aqueous solution doped with horseradish peroxidase and evaluated. As can be seen in FIG. 3, addition of iodide results in a reduction in the detection sensitivity of the test system with respect to horseradish peroxidase. In FIG. 3, the iodide concentration in the impregnation solution is plotted on the abscissa and the remission in % on the ordinate.

4. Practical Test on Various Samples of Heat-Treated Milk:

Test strips from Example 1 were dipped into milk heat-treated in various ways and analysed as described in Example 1. Samples with higher activity than in the measurement range were additionally diluted with peroxidase-free milk. The results are shown in FIG. 4. The heating temperature in ° C. is plotted along the abscissa. The high-temperature hold time was 20.2 seconds in each case. In order to obtain the second measurement point at 75.2° C. with lower activity, the high-temperature hold time was extended to 76.5 seconds. The ordinate indicates the remaining activity of the lactoperoxidase in U/l.

5. Practical Test on Vegetables and Cereals:

Analysis of Potatoes and Carrots 40 ml of demineralised water are added to 10 g of the material to be investigated, the mixture is chopped in a Moulinette, and the filtrate is further diluted as needed (depending on the peroxidase activity). 5 drops (about 0.25 ml) of 0.3% hydrogen peroxide solution are added to the sample solution, and the test strips are immediately immersed into the sample.

Result:

Using the example of a potato, a coloration which corresponds approximately to a value for milk of 5% of raw milk in peroxidase-free milk (see Example 1) was obtained after total dilution by a factor of 1:25. Using the example of a carrot, a coloration which corresponds approximately to a value for milk of 2.5% of raw milk in peroxidase-free milk (see Example 1) was obtained after total dilution by a factor of 1:25.

The invention claimed is:

1. A method for the determination of lactoperoxidase in milk or milk products, comprising:
   a) providing a sample comprising milk or milk products and a support to which at least one peroxidase substrate which gives a color upon reaction and an iodide have been applied; wherein the iodide has been applied to the support in a solution with a concentration between 1.5 and 8 mmol/l;
   b) immersing the support into the sample;
   c) waiting for a color reaction;
   d) detecting the color reaction.

2. The method according to claim 1, wherein the detection of said color reaction is carried out by reflectometry.

3. A method of determining the activity of lactoperoxidase in high-temperature-heated milk comprising carrying out the method of claim 1.

4. The method according to claim 1, wherein a non-support-stable reagent is added to said sample.

5. The method according to claim 4, wherein said reagent is hydrogen peroxide.

6. The method according to claim 4, wherein the non-support-stable reagent is a peroxide former.

7. The method according to claim 1, wherein the iodide concentration in the solution is between 3 and 4 mmol/l.

8. The method according to claim 1, wherein said substrate is 1,4-phenylenediamine, 2,2'-azinobis(3-ethylbenzothiazole-6-sulfonic acid) or 3,3',5,5'-tetramethylbenzidine.

9. The method according to claim 1, wherein the substrate and the iodide are embedded in a sorptive support.

10. The method according to claim 1, wherein said iodide is alkali metal iodide or ammonium iodide.

11. The method according to claim 1, wherein said iodide is lithium iodide.

* * * * *